United States Patent [19]
Kelly et al.

[11] Patent Number: 6,080,366
[45] Date of Patent: Jun. 27, 2000

[54] DISPOSABLE BLOOD TUBE HOLDER

[75] Inventors: Michael A. Kelly, York; Edward G. King, New Freedom, both of Pa.; Michael R. Walters, Baltimore; Bradley S. Thomas, Timonium, both of Md.

[73] Assignee: Becton, Dickinson and Company, Franklin Lakes, N.J.

[21] Appl. No.: 09/033,373

[22] Filed: Mar. 2, 1998

[51] Int. Cl.[7] .................................. B01L 3/14; A61B 5/14
[52] U.S. Cl. .......................... 422/102; 422/104; 422/100; 73/864.02
[58] Field of Search ..................................... 422/102, 104, 422/100; 73/864.02

[56] References Cited

U.S. PATENT DOCUMENTS

| | | |
|---|---|---|
| 3,199,775 | 8/1965 | Drucker . |
| 3,741,011 | 6/1973 | Seybold . |
| 3,955,890 | 5/1976 | Bessis et al. . |
| 4,027,660 | 6/1977 | Wardlaw et al. . |
| 4,077,396 | 3/1978 | Wardlaw et al. . |
| 4,082,085 | 4/1978 | Wardlaw et al. . |
| 4,156,570 | 5/1979 | Wardlaw . |
| 4,411,163 | 10/1983 | White . |
| 4,428,669 | 1/1984 | Bessis . |
| 4,436,631 | 3/1984 | Graham, Jr. et al. . |
| 4,479,720 | 10/1984 | Mochida et al. . |
| 4,555,183 | 11/1985 | Thomas . |
| 4,558,947 | 12/1985 | Wardlaw . |
| 4,567,754 | 2/1986 | Wardlaw et al. . |
| 4,683,058 | 7/1987 | Lyman et al. . |
| 4,774,965 | 10/1988 | Rodriguez et al. . |
| 4,823,624 | 4/1989 | Rodriguez et al. . |
| 4,848,917 | 7/1989 | Benin et al. . |
| 5,195,825 | 3/1993 | Ringrose . |
| 5,253,551 | 10/1993 | DeVaughn . |
| 5,380,087 | 1/1995 | Haber et al. . |
| 5,458,854 | 10/1995 | Burns . |
| 5,786,227 | 7/1998 | Charlton . |
| 5,924,594 | 7/1999 | Kelly . |

OTHER PUBLICATIONS

Stephen C. Wardlaw, MD, et al., "Quantitative Buffy Coat Analysis—A New Laboratory Tool Functioning as a Screening Complete Blood Cell Count", *Journal of the American Medical Association*, vol. 249, Feb. 4, 1983, pp. 617–620.

Robert L. Sallitt, et al., "Evaluation of Leukocyte Differential Counts on the QBC® Centrifugal Hematology Analyzer According to NCCLS Standard H20–T", *Blood Cells*, vol. 11, 1986, pp. 281–294.

QBC® Centrifugal Hematology Control Kit Brochure, Becton Dickinson and Company, 1988.

QBC® Autoread™ Centrifugal Hematology System Brochure, Becton Dickinson and Company, 1991.

QBC® Centrifuge System Centrifuge Model 424740 Brochure, Becton Dickinson and Company, Aug., 1993.

QBC® Centrifugal Hematology Control Brochure, Becton Dickinson and Company, 1995.

QBC® Hematology Control Assay, Becton Dickinson and Company, 1996.

QBC® Autoread™ Plus Brochure, Becton Dickinson and Company, 1996.

QBC® Hematology Control Instructions for Use, Becton Dickinson and Company, published prior to 1998.

*Primary Examiner*—Robert J. Warden, Sr.
*Assistant Examiner*—Jennifer C. McNeil
*Attorney, Agent, or Firm*—Bruce S. Weintraub

[57] ABSTRACT

A carrier tube system and method for using the same includes a carrier tube that is configured to receive a capillary blood tube, and a cap which seals the carrier tube to isolate the blood in the capillary tube from the surrounding atmosphere. The carrier tube system can be placed in a centrifuge which separates the blood with its component parts and optically reads the resulting layer thicknesses. The cap of the carrier tube can include a gear portion which is adapted for engagement with an indexing mechanism of the centrifuge, so that the indexing mechanism can rotate the carrier tube system about its longitudinal axis during centrifugation, thus allowing the optical reader of the centrifuge to take layer thickness readings at various positions about the circumference of the capillary tube. The cap can also include a float holder which holds a float that is inserted automatically into the capillary tube when the cap is placed.

17 Claims, 9 Drawing Sheets

DISPOSABLE BLOOD TUBE HOLDER

CROSS-REFERENCE TO RELATED APPLICATIONS

Related subject matter is disclosed and claimed in a copending U.S. patent application of Stephen C. Wardlaw entitled "Assembly for Rapid Measurement of Cell Layers", Ser. No. 08/814,536, filed on Mar. 10, 1997; in a copending U.S. Patent Application of Stephen C. Wardlaw entitled "Method for Rapid Measurement of Cell Layers", Ser. No. 08/814,535, filed on Mar. 10, 1997; in a copending U.S. patent application of Michael R. Walters entitled "Centrifugally Actuated Tube Rotator Mechanism" (Ser. No. 08/918, 437); in copending U.S. patent applications of Michael R. Walters entitled "Inertial Tube Indexer" and "Method for Using Inertial Tube Indexer", Ser. Nos. 09/032,931 and 09/033,367, filed on even date herewith; in copending U.S. patent applications of Bradley S. Thomas, Michael A. Kelley, Michael R. Walters, Edward M. Skevington and Paul F. Gaidis entitled "Blood Centrifugation Device With Movable Optical Reader"and "Method For Using Blood Centrifugation Device With Movable Reader", Ser. Nos. 09/033, 368 and 09/032,934; filed on even date herewith, and in a copending U.S. patent application of Bradley S. Thomas, entitled "Flash Tube Reflector With Arc Guide", Ser. No. 09/032,935, filed on even date herewith, all of said applications being expressly incorporated herein by reference.

BACKGROUND OF THE INVENTION

The present invention relates generally to a disposable device for holding a blood tube. More particularly, the present invention relates to a carrier tube which receives a blood tube and is capped to create a liquid-tight and aerosol-tight seal which isolates the contents of the blood tube from the outside environment. The carrier tube is adaptable for use with centrifuge-type blood count systems.

As part of a routine physical or diagnostic examination of a patient, it is common for a physician to order a complete blood count for the patient. The patient's blood sample may be collected in one of two ways. In the venous method, a syringe is used to collect a sample of the patient's blood in a test tube containing an anticoagulation agent. A portion of the sample is later transferred to a narrow glass sample tube such as a capillary tube. The open end of the sample tube is placed in the blood sample in the test tube, and a quantity of blood enters the sample tube by capillary action. The sample tube has two fill lines at locations about its circumference, and the volume of blood collected should reach a level in the sample tube between the two fill lines. In the capillary method, the syringe and test tube are not used, and the patient's blood is introduced directly into the sample tube from a small incision made in the skin. In either case, the sample tube is then placed in a centrifuge, such as the Model 424740 centrifuge manufactured by Becton Dickinson and Company.

In the centrifuge, the sample tube containing the blood sample is rotated at a desired speed (typically 8,000 to 12,000 rpm) for several minutes. The high speed centrifugation separates the components of the blood by density. Specifically, the blood sample is divided into a layer of red blood cells, a buffy coat region consisting of layers of granulocytes, mixed lymphocytes and monocytes, and platelets, and a plasma layer. The length of each layer can then be optically measured, either manually or automatically, to obtain a count for each blood component in the blood sample. This is possible because the inner diameter of the sample tube and the packing density of each blood component is known, and hence the volume occupied by each layer and the number of cells contained within it can be calculated based on the measured length of the layer. Exemplary measuring devices that can be used for this purpose include those described in U.S. Pat. Nos. 4,156,570 and 4,558,947, both to Stephen C. Wardlaw, and the QBC® "AUTOREAD" centrifuged hematology system manufactured by Becton Dickinson and Company.

Several techniques have been developed for increasing the accuracy with which the various layer thickness in the centrifuged blood sample can be determined. For example, because the buffy coat region is typically small in comparison to the red blood cell and plasma regions, it is desirable to expand the length of the buffy coat region so that more accurate measurements of the layers in that region can be made. As described in U.S. Pat. Nos. 4,027,660, 4,077,396, 4,082,085 and 4,567,754, all to Stephen C. Wardlaw, and in U.S. Pat. No. 4,823,624, to Rodolfo R. Rodriguez, this can be achieved by inserting a precision-molded plastic float into the blood sample in the sample tube prior to centrifugation. The float has approximately the same density as the cells in the buffy coat region, and thus becomes suspended in that region after centrifugation. Since the outer diameter of the float is only slightly less than the inner diameter of the sample tube (typically by about 80 $\mu$m), the length of the buffy coat region will expand to make up for the significant reduction in the effective diameter of the tube that the buffy coat region can occupy due to the presence of the float. By this method, an expansion of the length of the buffy coat region by a factor between 4 and 20 can be obtained. The cell counts calculated for the components of the buffy coat region will take into account the expansion factor attributable to the float.

Another technique that is used to enhance the accuracy of the layer thickness measurements is the introduction of fluorescent dyes (in the form of dried coatings) into the sample tube. When the blood sample is added to the sample tube, these dyes dissolve into the sample and cause the various blood cell layers to fluoresce at different optical wavelengths when they are excited by a suitable light source. As a result, the boundaries between the layers can be discerned more easily when the layer thickness are measured following centrifugation.

Typically, the centrifugation step and the layer thickness measurement step are carried out at different times and in different devices. That is, the centrifugation operation is first carried out to completion in a centrifuge, and the sample tube is then removed from the centrifuge and placed in a separate reading device so that the blood cell layer thicknesses can be measured. More recently, however, a technique has been developed in which the layer thicknesses are calculated using a dynamic or predictive method while centrifugation is taking place. This is advantageous not only in reducing the total amount of time required for a complete blood count to be obtained, but also in allowing the entire procedure to be carried out in a single device. Apparatus and methods for implementing this technique are disclosed in the aforementioned copending U.S. patent applications of Stephen C. Wardlaw entitled "Assembly for Rapid Measurement of Cell Layers", Ser. No. 08/814,536 which has issued as U.S. Pat. No. 5,889,581 and "Method for Rapid Measurement of Cell Layers", Ser. No. 08/814,535 which has issued as U.S. Pat. No. 5,888,184.

In order to allow the centrifugation and layer thickness steps to be carried out simultaneously, it is necessary to freeze the image of the sample tube as it is rotating at high speed on the centrifuge rotor. This can be accomplished by means of a xenon flash lamp assembly that produces, via a lens and a bandpass filter, an intense excitation pulse of blue light energy (at approximately 470 nanometers) once per revolution of the centrifuge rotor. The pulse of blue light excites the dyes in the expanded buffy coat area of the sample tube, causing the dyes to fluoresce with light of a known wave length. The emitted fluorescent light resulting from the excitation flash is focused by a high-resolution lens onto a linear CCD array. The CCD array is located behind a bandpass filter which selects the specific wavelength of emitted light to be imaged onto the CCD array.

The xenon flash lamp assembly is one of two illumination sources that are focused onto the sample tube while the centrifuged rotor is in motion. The other source is an array of light-emitting diodes (LEDs) which transmits red light through the sample tube for detection by the CCD array through a second band pass filter. The purpose of the transmitted light is to initially locate the beginning and end of the plastic float (which indicates the location of the expanded buffy coat area), and the fill lines. Further details of the optical reading apparatus may be found in the aforementioned copending application of Michael R. Walters entitled "Inertial Tube Indexer", Ser. No. 09/032,931, and in the aforementioned copending application of Bradley S. Thomas et al., entitled "Blood Centrifugation Device with Movable Optical Reader", Ser. No. 09/033,368.

Several problems exist with using a standard sample tube in a centrifugation device of the type described above. In particular, because the tube is made of glass, it is possible for the tube to shatter either during handling or during centrifugation if the tube is not properly handled or loaded. If this occurs, the blood sample in the tube can come in contact with the person handling the tube, or can become airborne if the tube is being centrifuged. Therefore, any pathogen that may be present in the blood sample can be spread to people in the immediate area of the centrifuge device. Also, the shattered tube can result in injury due to sharp edges or flying glass.

Furthermore, in the centrifuging techniques described above, the sample tube is not sealed prior to centrifugation. Hence, infectious agents that may exist in the blood sample can possibly become airborne during centrifugation even if the tube does not break.

Although it is possible to coat the sample tube with a shatterproofing material, this drastically increases the cost of the sample tube while only slightly improving safety. Furthermore, this technique does not positively isolate the blood sample in the tube from the outside atmosphere. As a result, some of the blood sample can still escape during centrifugation.

Accordingly, a continuing need exists for a technique which will obviate the above problems associated with standard glass sample tubes without redesigning or changing the physical makeup of the tube.

SUMMARY OF THE INVENTION

An object of the present invention is to provide a cost-effective device which safeguards against potential damage that can occur due to the shattering of a standard sample tube during handling or centrifugation.

A further object of the invention is to isolate the sample in the sample tube from the atmosphere during centrifugation to provide an aerosol-free environment in the centrifuge.

A further object of the invention is to provide a device which enables the sample tube to be used in a centrifuge device that is capable of centrifuging the blood sample and simultaneously reading the layers in the centrifuged blood sample, while rotating the sample tube about its longitudinal axis to obtain a more accurate measurement of the lengths of the separated layers.

These and other objects of the present invention are substantially achieved by providing a carrier system for use with a blood tube, comprising a carrier tube having a chamber therein and an opening at a first end thereof for providing access to the chamber, such that the chamber is configured to receive a blood tube through the opening. The carrier system further comprises a cap which is configured to be coupled to the first end of the carrier tube to substantially isolate the blood tube from the atmosphere outside the carrier tube.

The cap of the carrier system preferably includes a float which is removably coupled thereto, such that the float enters the blood tube when the cap is coupled to the first end of the carrier tube. The cap may also include a geared portion which is configured to engage with an indexing member of a centrifuge device, so that the indexing member can rotate the carrier system about its longitudinal axis while the centrifuge device reads the layer thickness in the centrifuged blood sample in the blood tube.

BRIEF DESCRIPTION OF THE DRAWINGS

These and other objects of the invention will be more readily appreciated from the following detailed description when read in conjunction with the accompanying drawings, in which.

DETAILED DESCRIPTION OF THE PREFERRED EMBODIMENTS

Figure 1:
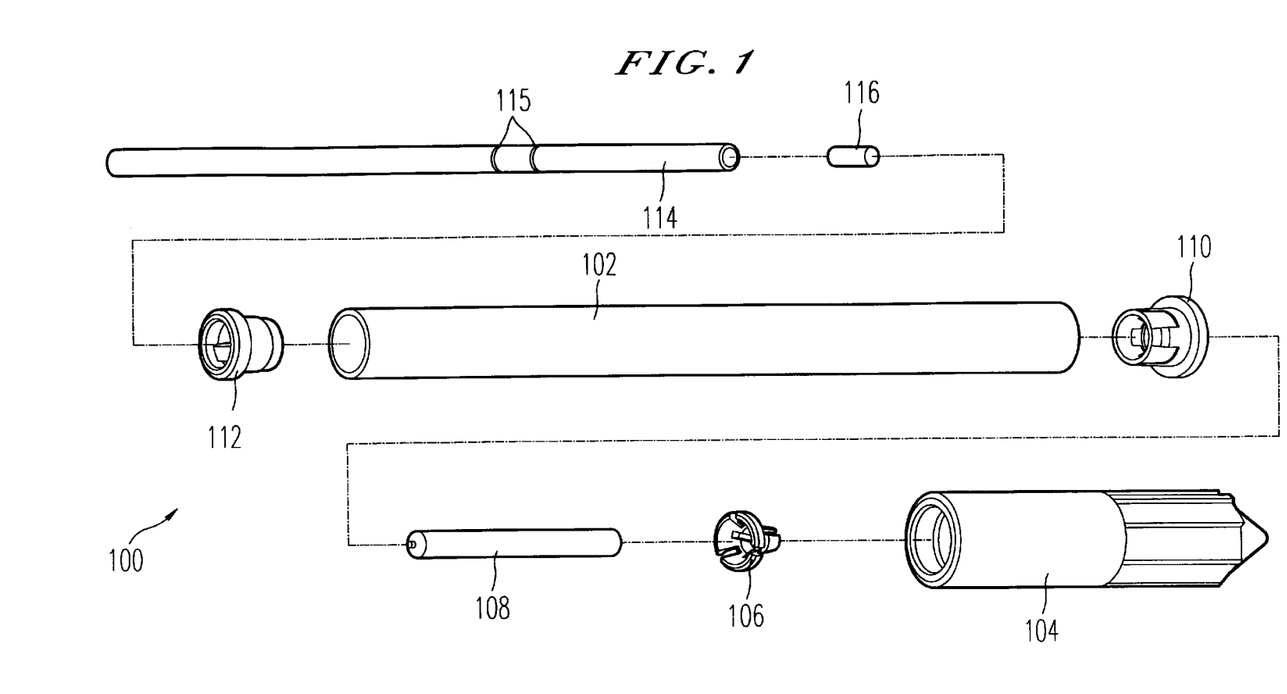
FIG. 1 is an exploded perspective view of a carrier system for a blood tube according to an embodiment of the present invention.
Figure 2:
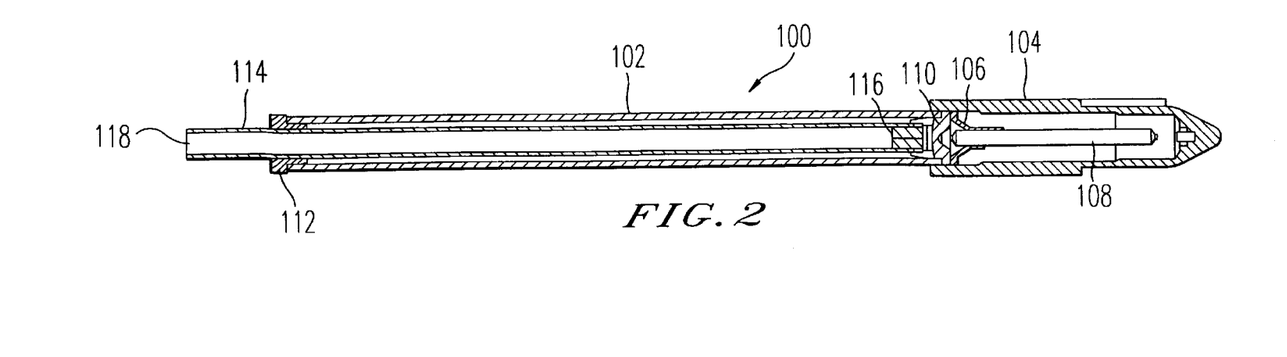
FIG. 2 is a side sectional view showing the carrier system of FIG. 1 in its assembled condition prior to use.

A carrier tube system 100 according to an embodiment of the present invention is illustrated in FIGS. 1 and 2. As illustrated, the carrier tube system includes a carrier tube 102, a cap 104, a float holder 106, a float 108, a bottom plug 110, a top collar 112, and a capillary tube 114 having two fill lines 115 about its circumference as shown, and a plug 116 inserted therein. As illustrated specifically in FIG. 2, and as will be described below, when the carrier tube system 100 is assembled prior to use, the bottom plug 110 and top collar 112 are inserted and secured to opposite ends of the carrier tube 102 by a suitable adhesive. The plug 116 is secured in the capillary tube 114 by an interference fit, and the capillary tube 114 containing the plug 116 is inserted through an opening in the top collar 112 into the carrier tube 102.

As further illustrated, the float holder 106 is inserted into the cap 104, and the float 108 is inserted into the float holder 106 so that both the float holder and float are retained in the cap 104. The cap is removably coupled to the bottom end of the carrier tube 102 at which the bottom plug 110 is inserted. Hence, the configuration shown in FIG. 2 can be considered the initial uncapped configuration of the carrier tube system. In this configuration, the end 118 of the capillary tube 114 remains open and ready to receive blood.

The carrier tube system 100 in the uncapped state shown in FIG. 2 can be sterilized and sealed in, for example, a sterile foil pouch for transport to a medical laboratory at which the carrier tube system 100 will be used. At the laboratory, the capillary tube 114 is used to collect a sample of blood so that a complete count of the blood can be taken. As will be described in more detail below, after the blood is drawn into the capillary tube 114, the cap 104, and the float holder 106 and float 108 retained therein, are transferred to the top end of the carrier tube 102 to seal the opening 118 in the capillary tube 114.

Figure 3:
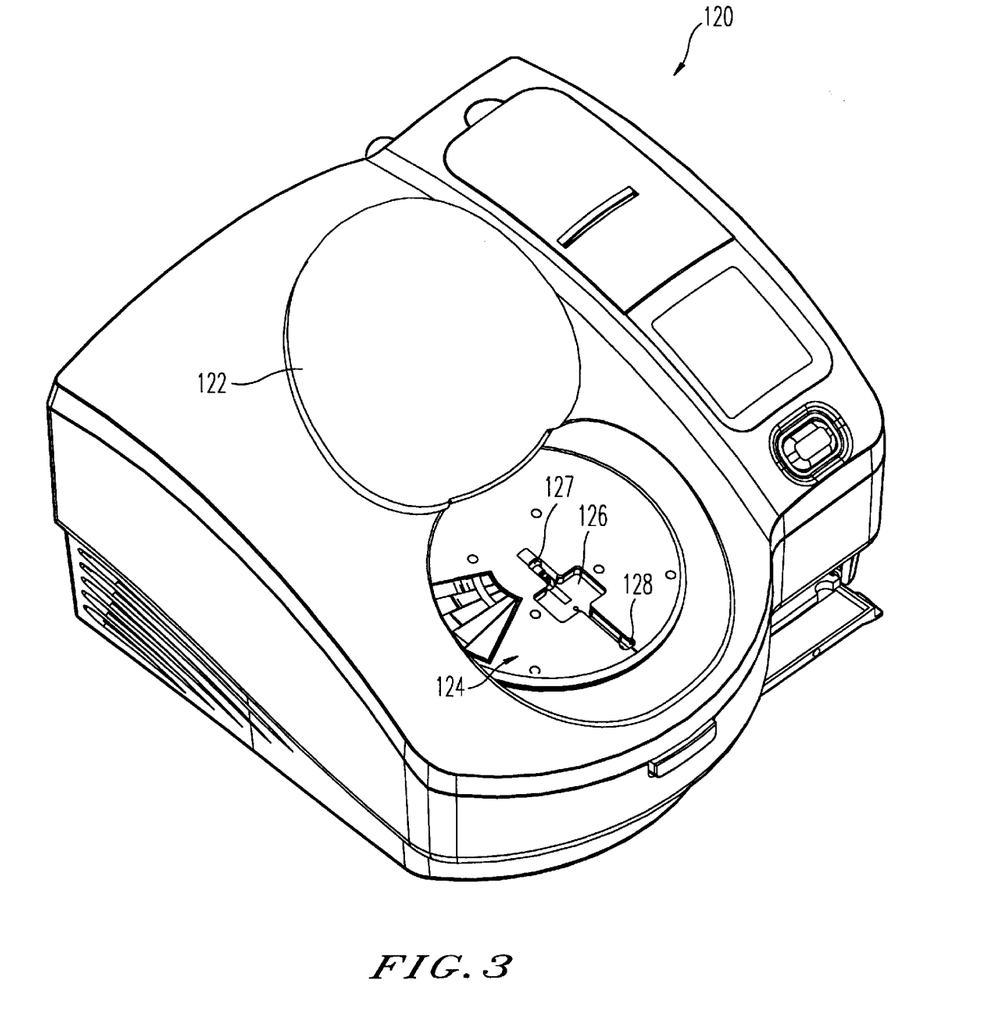
FIG. 3 is a perspective view of a centrifuge device in which the carrier system shown in FIG. 1 can be used.
Figure 4:
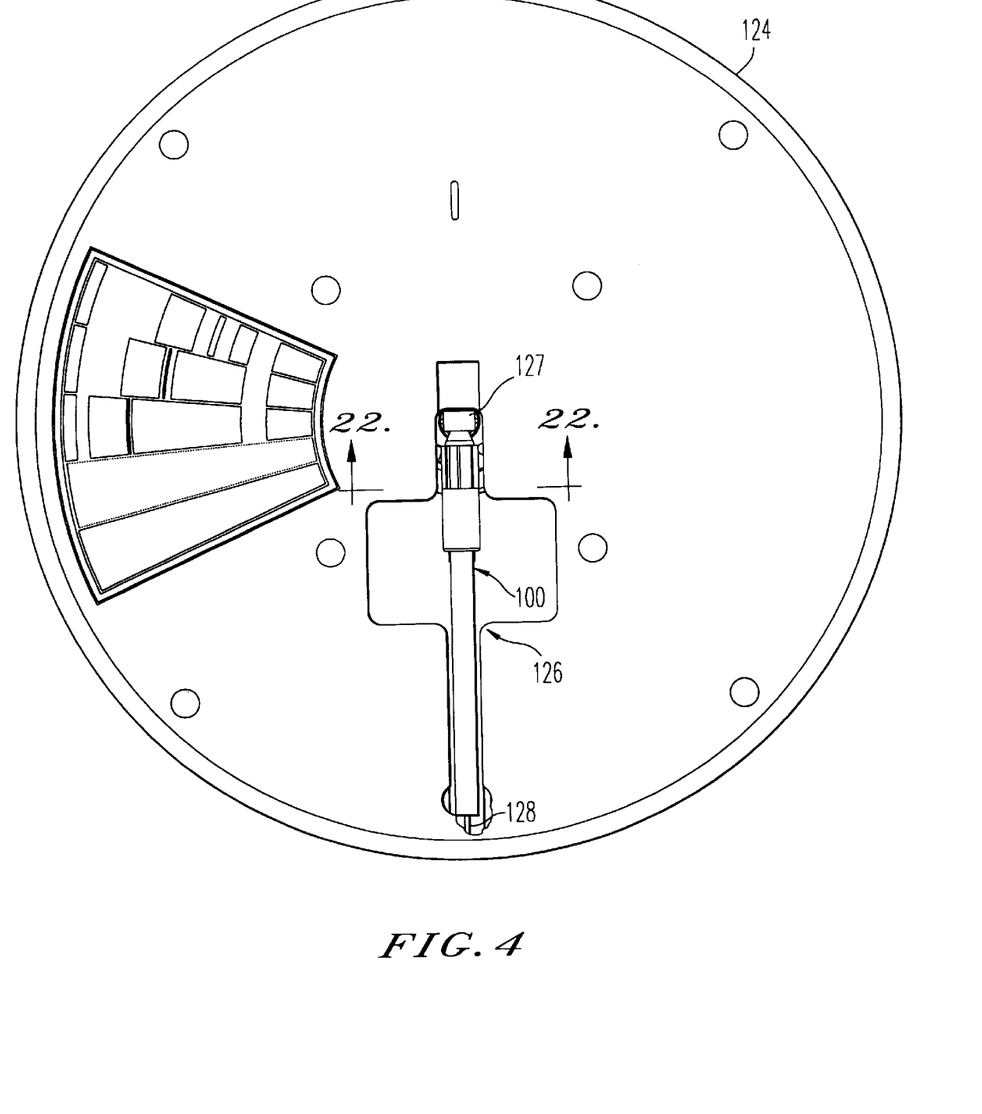
FIG. 4 is a detailed perspective view of the rotor of the centrifuge device shown in FIG. 3, with the carrier tube system of FIG. 1 inserted therein.

The carrier tube system 100 in its capped state is shown generally in FIGS. 3 and 4 in relation to a centrifuge apparatus 120 that is used to centrifuge the blood sample stored in the capillary tube 114 to separate the components of the blood into individual layers so that a complete blood count can be taken. As shown in FIG. 3 and as described in more detail below, the door 122 of the centrifuge device 120 can be opened to allow access to the rotor 124 of the centrifuge device 120. As shown specifically in FIG. 4, the carrier tube system 100 in its capped state is placed into a tube-receiving recess 126 in the rotor 124. Specifically, the rotor 124 includes a cap-receiving cup 127 and a pin 128 which secure the carrier tube system 100 in the rotor 124 as will be describe in more detail below. The door 122 can then be closed and the carrier tube system 100 can be centrifuged by the apparatus 120 to separate the blood components into the layers described above.

Figure 5:
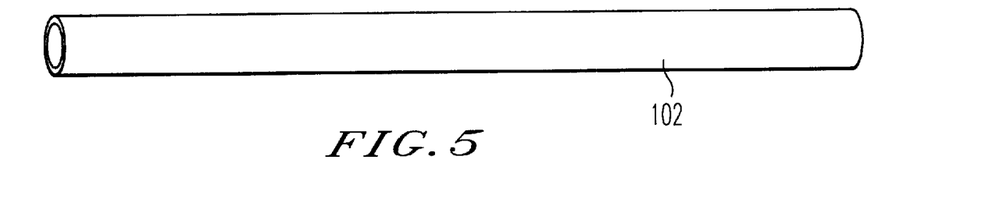
FIG. 5 is a detailed perspective view of the carrier tube used in the carrier tube system of FIG. 1.
Figure 6:
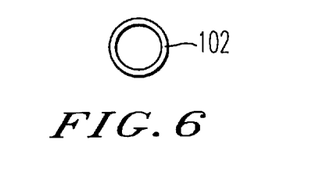
FIG. 6 is a cross-sectional view of the carrier tube shown in FIG. 5.

The details of the carrier tube system and its components will now be described. As shown in FIGS. 5 and 6, the carrier tube 102 is preferably in the form of a cylindrical tube that is made of a transparent plastic material, such as polyvinylchloride, acrylic, polycarbonate or the like. The diameter of the tube 102 must be sufficient to receive a standard capillary tube, such as the capillary tube 114. The inner diameter of the tube 102 can be, for example, about 0.140 inch, while the outer diameter can be, for example, about 0.180 inch. The length of the tube 102 is preferably such that a portion of a standard capillary tube 114 projects from the open end of the carrier tube 102 when the capillary tube 114 is received in carrier tube 102, as shown in FIG. 2.

Figure 7:
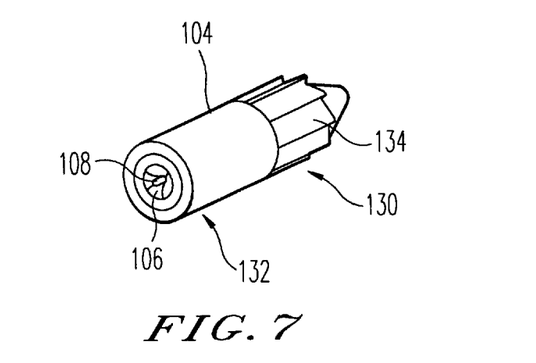
FIG. 7 is a detailed perspective view of the cap assembly used in the carrier tube system of FIG. 1 with the float holder and float installed.
Figure 8:
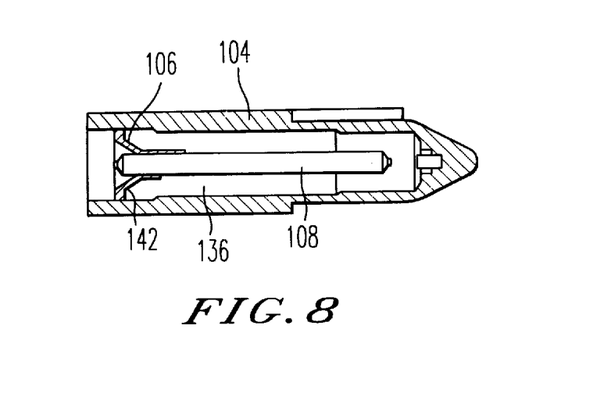
FIG. 8 is a cross-sectional view of the cap assembly shown in FIG. 7.

The details of the cap 104, float 108, and float holder 106 are shown more clearly in FIGS. 7 and 8. The cap 104 can be made of a plastic material such as polypropylene, polyethylene, or the like, and should be semi-transparent to view the blood fill level, especially after that level has increased when the float 108 has been inserted. The cap 104 is generally cylindrical and includes a gear portion 130 and a substantially smooth cylindrical portion 132. The gear portion 130 includes a plurality of gear teeth 134 which are formed evenly about the circumference of the cap 104. The gear teeth 134 are configured to engage with an engaging member of the centrifuge rotor 124 (see FIGS. 3 and 4), as will be discussed in more detail below.

The cap 104 includes an inner cylindrical cavity 136 which is configured to receive the float holder 106 and float 108. The diameter of the inner cavity 136 is sufficient to allow cap 104 to be coupled to the outside of the tube 102 by means of a friction fit, as shown in FIG. 2. Because the cap 104 is made of a resilient plastic material, the cap can expand as necessary to receive the end of the carrier tube 102 having the plug 110, and thus engage that end of the carrier tube 102.

Figure 9:
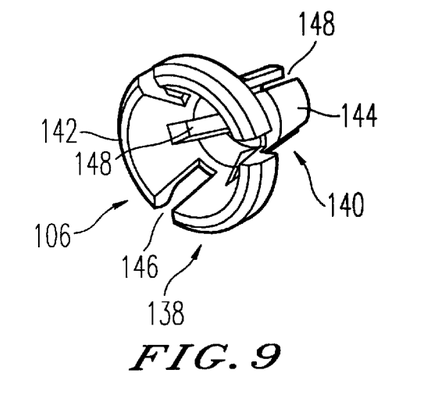
FIG. 9 is a detailed perspective view of the float holder which is inserted into the cap used in the carrier system of FIG. 1.
Figure 10:
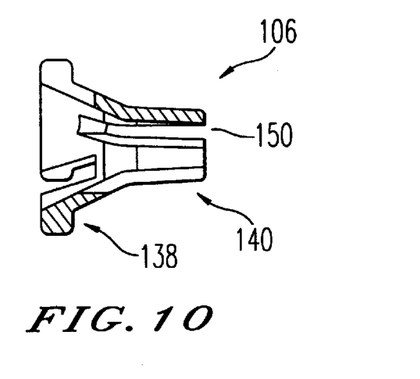
FIG. 10 is a cross-sectional view of the float holder shown in FIG. 9.

The float holder 106 is shown in more detail in FIGS. 9 and 10. Specifically, the float holder includes a conical portion 138 and a substantially cylindrical portion 140. The conical portion 138 includes a plurality of arcuate sections 142 which are integrally molded to each other and to a plurality of arcuate sections 144 forming the substantially cylindrical portion 140 of the float holder 106. The sections 142 are separated from each other by spaces 146, and the sections 144 are separated from each other by spaces 148 which are offset from the spaces 146 as shown. The float holder 106 is made of a resilient plastic material, such as polyethylene, polypropylene, or the like. This sectional configuration of the float holder 106 provides added expansion and contraction capabilities.

The float holder 106 further includes an opening 150 passing longitudinally therethrough, and which is formed by the sections 142 and 144. As shown in FIG. 8, the float 108 is received in the opening 150. The sections 144 are resiliently deformed by the float 108, and grip the float 108 about its circumference to thus hold the float 108 in the float holder 106. As described in more detail below, the sections 144 grip the float 108 firmly enough to prevent the float 108 from falling out of the float holder 106 inadvertently, but allow the float 108 to release when capillary tube 114 slips over the float 108 and spreads sections 114, thus breaking contact between float 108 and float holder 106.

As shown in FIG. 8, the sections 142 of the float holder 106 are elastically deformable when the float holder 106 is inserted into the cavity 136 of the cap 104. The sections 142 thus exert a force against the inner walls of cap 104 that is sufficient to maintain the float holder 106 and the float 108 inside the cap 104. However, as will be described in more detail below, when a force is applied longitudinally against the float holder 106, the sections 142, and hence the float holder 106, as a whole, can slide along the inner walls of the cap 104.

Figure 11:
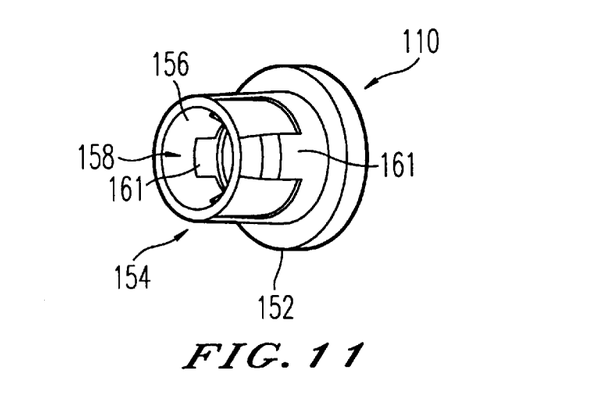
FIG. 11 is a detailed perspective view of the bottom carrier plug used in the system of FIG. 1.
Figure 12:
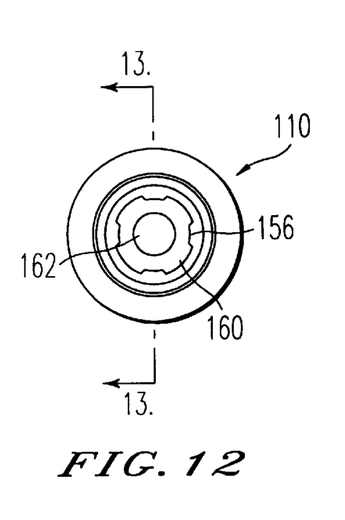
FIG. 12 is a top plan view of the bottom carrier plug shown in FIG. 11.
Figure 13:
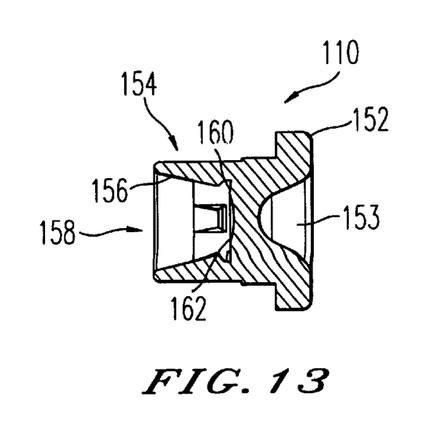
FIG. 13 is a cross-sectional view of the bottom carrier plug as taken along lines 13—13 in FIG. 12.

FIGS. 11–13 illustrate the bottom plug 110 in more detail. As shown, the bottom plug 110 includes a disk-shaped portion 152 having a recess 153 therein, and a substantially cylindrically portion 154 that is integral with the disk-shaped portion 152. The purpose of the recess 153 is described below. The bottom plug 110 is formed of a resilient plastic material, such as polyvinylchloride or the like. The substantially cylindrical portion 154 includes inwardly projecting members 156 that project into a recess 158 formed in the substantially cylindrical portion 154. As shown, for example, in FIGS. 1 and 2, the bottom plug 110 is secured to the carrier tube 102 in a manner such that the substantially cylindrical portion 154 is received in the inner chamber of the carrier tube 102. The substantially cylindrical portion 154 can be secured to the inner wall of the carrier tube 102 by a suitable adhesive. As illustrated in FIG. 2, the diameter of the disk-shaped portion 152 of the bottom plug 110 can be slightly greater than the outer diameter of the carrier tube 102. This configuration provides a more secure gripping of the interior walls of the cap 104 when the cap 104 is releasably coupled to the bottom end of the tube 102.

As shown in FIG. 12, the projecting members 156 of the bottom plug 110 are integrally coupled to a bottom surface 160. Further, spaces 161 exist between the projecting members 156. As indicated, the bottom surface 160 is inclined such that the portions of the bottom surface 160 which contact the projecting members 156 extend deeper into the recess 158, and the bottom surface 160 thus has a generally convex shape in the recess 158. The purpose of this convexity is to seal the capillary tube 114 so that leakage of blood through the plug 116 does not occur during centrifugation. A concave portion 162 exists at the center or substantially at the center of the bottom surface 160. The concave portion 162 is formed as a result of the manufacturing process used to make the bottom plug 110, and has no significant function.

Figure 14:
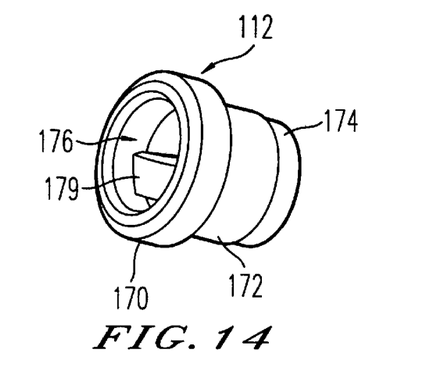
FIG. 14 is a detailed perspective view of the top carrier collar used in the system of FIG. 1.
Figure 15:
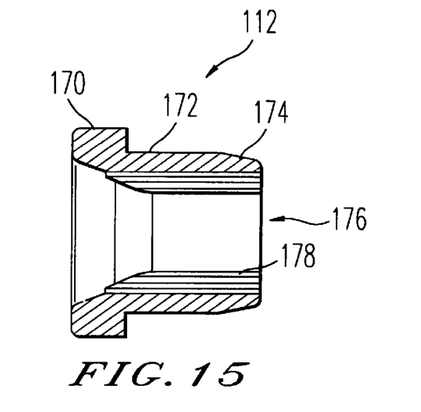
FIG. 15 is a cross-sectional view of the top carrier collar shown in FIG. 14.

The top collar 112 of the carrier tube assembly 100 is shown in more detail in FIGS. 14 and 15. The top collar 112 includes a large diameter portion 170 and a narrower diameter portion 172. The narrower diameter portion includes a tapered portion 174 which facilitates insertion of the narrow diameter portion 172 of the collar 112 into the top of the carrier tube 102 as shown, for example, in FIG. 2. As with the bottom plug 110, the top collar 112 can be secured in the carrier tube 102 by any suitable adhesive. As illustrated, the diameter of the large-diameter portion 170 of the top collar 112 should be slightly greater than the outer diameter of the carrier tube 102 to provide a seal between the carrier tube 102 and cap 104 when the cap 104 is capped onto this end of the carrier tube 102 as described below. The top collar 112 further includes an opening 176 passing through the center thereof. Projecting members 178 project into the opening 176 as shown, and recesses 179 are present between the projecting members 178, to allow air to escape from the interior of the carrier tube 102 to enhance capillary action of the blood entering the capillary tube 114 when the capillary tube 114 is being filled as described in more detail below.

As shown in FIG. 2, when the capillary tube 114 is inserted into the carrier tube 102 that has been assembled with the bottom plug 110 and top collar 112, the projecting members 178 of the top collar 112 and the projecting members 156 of the bottom plug 110 grip the outside of the capillary tube 114 to secure the capillary tube 114 in the carrier tube 102. Since the projecting members 178 of the top collar 112 and the projecting members 156 of the bottom cap 110 are resiliently deformable (as are the top and bottom caps 110 and 112 themselves), the projecting members 156 and 178 exert a force against the capillary tube 114 that is sufficient to maintain the capillary tube in the carrier tube 102 and to resist movement of the capillary tube 114 along its longitudinal axis.

Figure 16:
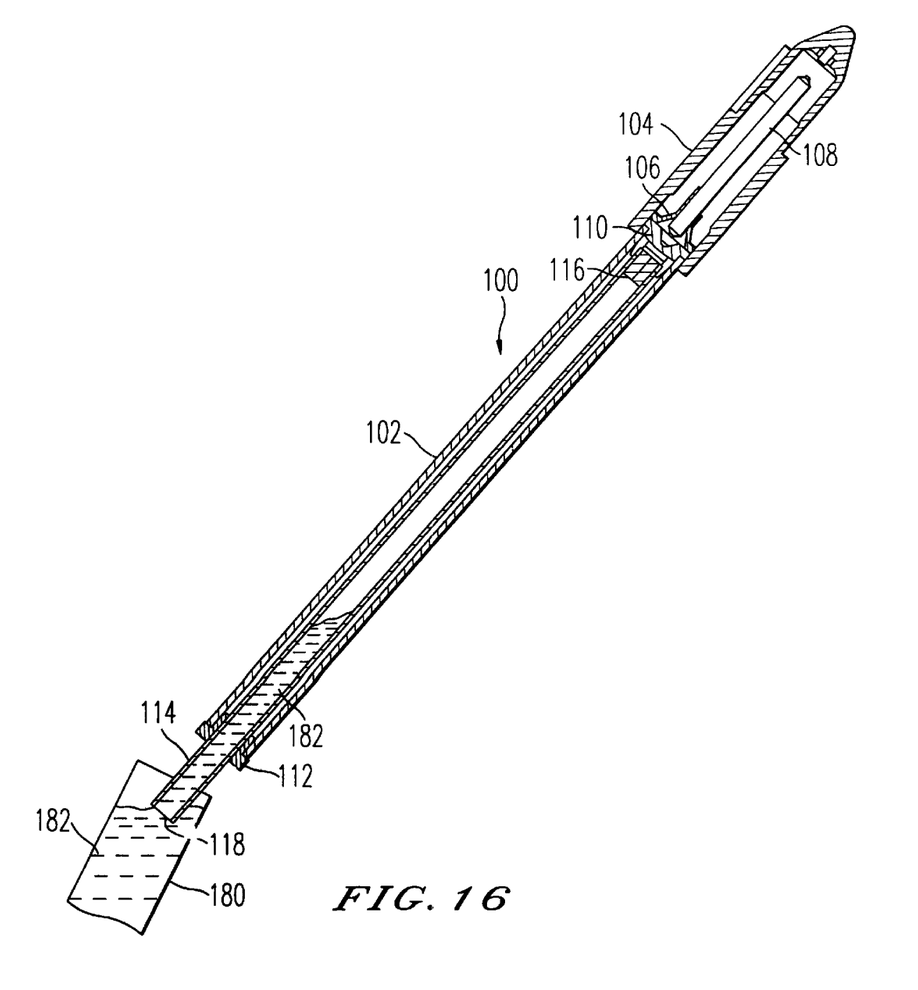
FIG. 16 is a cross-sectional view of the carrier system shown in FIG. 1 being used to collect a blood sample, with the cap attached to the bottom end of the carrier tube.

The operation of the carrier tube 100 will now be described with reference to FIGS. 16–21. As described above with regard to FIG. 2, when the carrier tube system 100 is in the uncapped state with the cap 104 coupled to the bottom end of the carrier tube 102, the carrier tube system 100 can be sterilized and packaged in a sterile foil pouch or other container for shipment to a medical laboratory. At the laboratory, a technician opens the sterile pouch and removes the carrier tube system 100. The technician then transfers a blood sample in the capillary tube 114 by placing the open end 118 of the capillary tube 114 directly at an incision or puncture in the skin of the patient from which the blood sample is being taken, or by obtaining the sample from a collection tube 180 in which uncoagulated blood 182 that has been taken from the patient is being stored. This latter operation is illustrated in FIG. 16.

Figure 17:
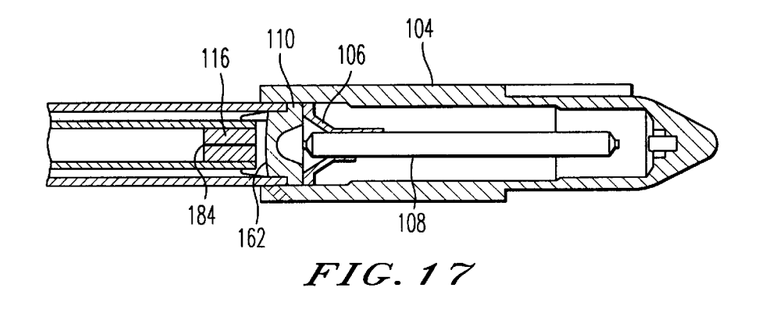
FIG. 17 is a detailed cross-sectional view of the carrier system shown in FIG. 1, with the cap attached to the bottom end of the carrier tube.

As shown in FIG. 17, the capillary tube plug 116 has a longitudinal opening 184 therein, which is about 0.006 inch in diameter. The opening 184 permits gas inside the capillary tube 114 to escape as the blood 182 enters the capillary tube 114 through the open end 118, and thus facilitates the entry of the blood 182 into the capillary tube 114 by capillary action. As further illustrated, the projecting members 156 of the bottom plug 110 maintains the capillary tube 114 at a predetermined distance from the bottom surface 160 inside the recess 158 of the plug. Due to the presence of spaces 161 between the projecting portions 156 as shown in FIG. 11, the gas that passes out of the opening 184 in the plug 116 passes through spaces 161 and thus into the interior of the carrier tube 102. The gas can then pass between the inner wall of the carrier tube 102 and the outer wall of the capillary tube 114, through the recesses 179 in the top plug 112, and thus out of the carrier tube system 100 and into the surrounding atmosphere. The plug 116 can be a self-sealing type plug fabricated from a hydrophilic material or a Porex material which swells when contacted by the blood to close opening 184.

Figure 18:
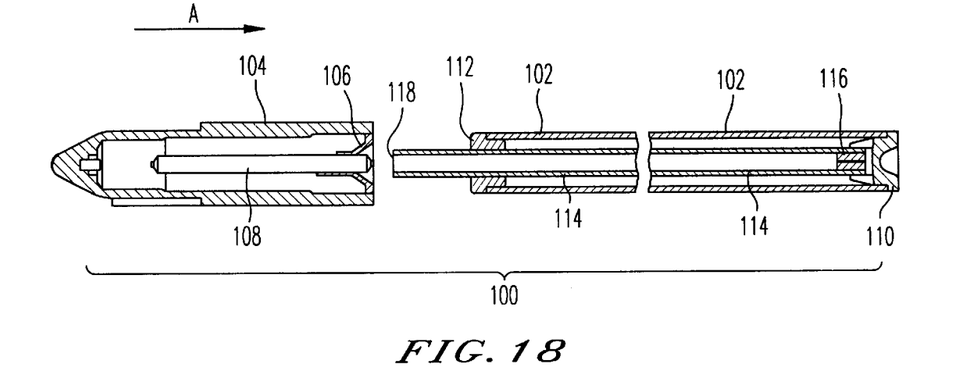
FIG. 18 is a cross-sectional view of the carrier system shown in FIG. 1, with the cap being aligned for coupling to the top end of the carrier tube.

Once a suitable amount of blood has been received in the capillary tube 114 (i.e., the level of blood is between fill lines 115), the carrier tube system can be configured for insertion into the centrifuge device 120 as shown in FIGS. 3 and 4. Specifically, as shown in FIG. 18, the cap 104 is removed from the bottom end of the carrier tube 102 and is placed in substantial alignment with the top end of the carrier tube 102 from which the capillary tube 114 projects. The cap is then moved the direction shown by the arrow A toward the top of the carrier tube 102.

Figure 19:
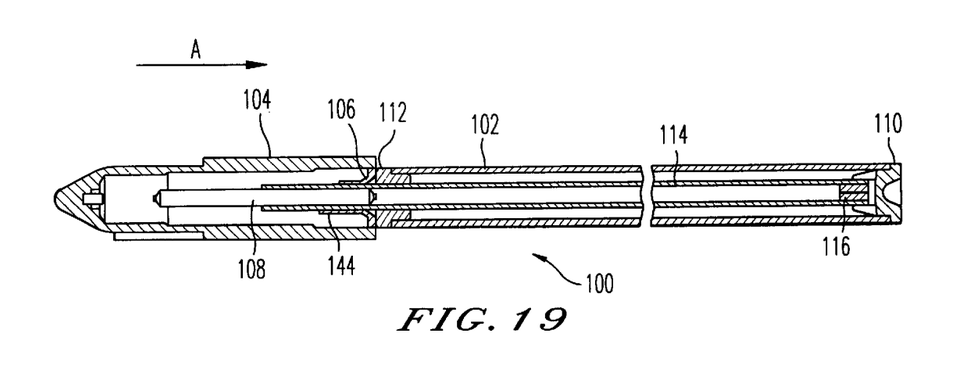
FIG. 19 is a cross-sectional view showing the cap being coupled to the top end of the carrier tube and the float being inserted into the capillary tube.

As shown in FIG. 19, as the cap moves closer to the carrier tube 102, the float holder 106 begins to engage the capillary tube 114. The conical portion 138 of the tube holder 160 shown in FIG. 9, assists in aligning the capillary tube 114 with the substantially cylindrical portion 140 of the float holder 106 so that the capillary tube 114 begins to pass into opening 150 of the float holder 106. Because the float holder 106 holds the float 108 such that a portion of the float 108 projects into the recess of the conical shaped portion 138 of the float holder 106, the float 108 begins to enter the capillary tube 114. As the cap 104 is further advanced toward the carrier tube 102, the capillary tube 114 advances further into the opening 150 in the float holder 106. Because the sections 144 of the float holder 106 which define the opening 150 are resilient, and the diameter of the opening 150 is smaller than the outer diameter of the capillary tube 114, the capillary tube 114 will begin to force the sections 144 radially outward. Hence, the capillary tube 114 begins to capture the float 108 as the sections 144 release the float 108. It is noted that the bottom plug 110 and top collar 112 of the carrier tube 102 maintain the capillary tube 114 substantially in its original position so that the capillary tube 114 does not move appreciably along its longitudinal axis.

Figure 20:
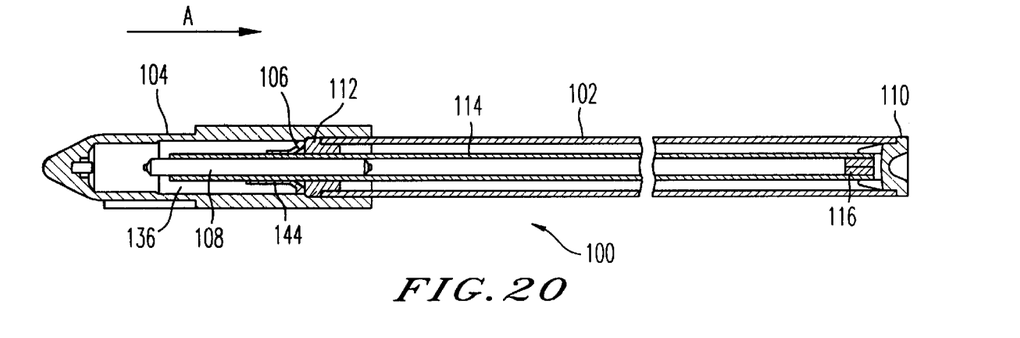
FIG. 20 is a cross-sectional view illustrating the cap being further inserted onto the top end of the carrier tube and the float further entering the capillary tube.

As shown in FIG. 20, as the cap 104 is moved further in the direction of arrow A, the interior chamber 136 of the cap 104 begins to receive the top end of the carrier tube 102 in which the collar 112 has been inserted. As a result, the collar 112 contacts the float holder 106 and begins to move the float holder 106 in a direction opposite to that indicated by arrow A. The interior surfaces of the sections 144 of the float holder 106 contact and thus slide along the outer surface of the capillary tube 114. As this occurs, the float 108 is received further into the capillary tube 114.

Figure 21:
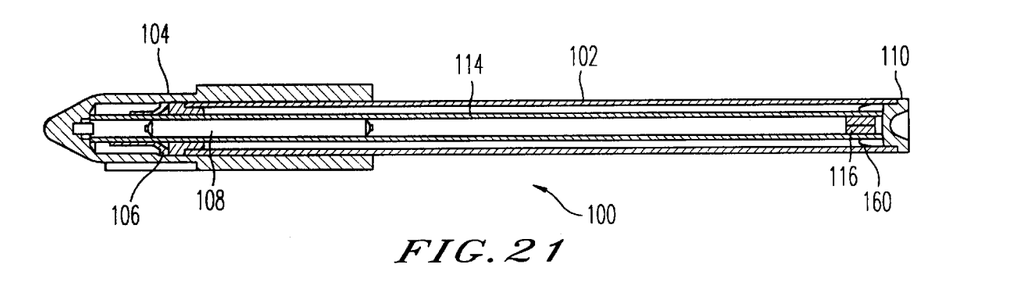
FIG. 21 is a cross-sectional view of the system shown in FIG. 1 with the cap being fully inserted onto the top end of the carrier tube and the float being contained in the capillary tube.

FIG. 21 illustrates the carrier tube system 100 with the cap 104 in its fixed position on the top end of carrier tube 102. To reach this position, the cap 104 has moved further in the direction of arrow A in FIG. 19, so that the open end 118 of the capillary tube 114 abuts against the interior top surface of the cap 104. Once this occurs, movement of the cap in the direction of arrow A exerts a force in the longitudinal direction the of capillary tube 114 sufficient to overcome the gripping strength of projecting members 156 and 178 of the bottom plug 110 and top collar 112, respectively. As a result, the capillary tube 114 slides against the projecting members 156 and 178 in the direction along arrow A until the bottom of the capillary tube 114 at which the plug 116 is positioned abuts against the bottom surface 160 of the bottom plug 110. In this condition, the bottom surface 160 creates a seal which obstructs the opening 184 and does not permit air or blood to flow out of the opening 184. It is noted that the convex shape of the bottom surface 160 provides a better seal for the opening 184 in the event that the capillary tube 114 is slightly misaligned with the central axis of the bottom plug 110.

When the carrier tube system 100 is configured as shown in FIG. 21, the carrier tube system 100 is ready for placement into the tube-receiving cavity 126 of the rotor 124 of the centrifuge device 120 as shown in FIGS. 3 and 4. Specifically, as shown in more detail in FIG. 4, the nose of the cap 104 is received into a cap-receiving cup 127, while a pin 128 carried by the rotor 124 is received into the recess 153 of the bottom plug 110 of the carrier tube system 100. The manner in which the carrier tube system 100 is received in the rotor 124 is described in more detail in the aforementioned copending U.S. patent application of Michael R. Walters entitled "Inertial Tube Indexer", Ser. No. 09/032, 931, and in the aforementioned copending U.S. patent application of Bradley S. Thomas et al. entitled "Blood Centrifugation Device with Movable Optical Reader", Ser. No. 09/033,368.

It is noted that in the event that the capillary tube 114 fractures, the float holder 106 limits the depth that the carrier tube 102 can enter the interior chamber 136 of the cap 104, thereby limiting the amount that the overall length of the carrier tube system 100 can decrease. This prevents the overall length of the carrier tube system 100 from decreasing due to possible sliding of the carrier tube 102 further into the interior chamber 136 of the cap 104 during spinning of the rotor 124, which could result in the carrier tube system 100 disengaging with the cap-receiving cup 127 and being ejected from the rotor 124.

Figure 22:
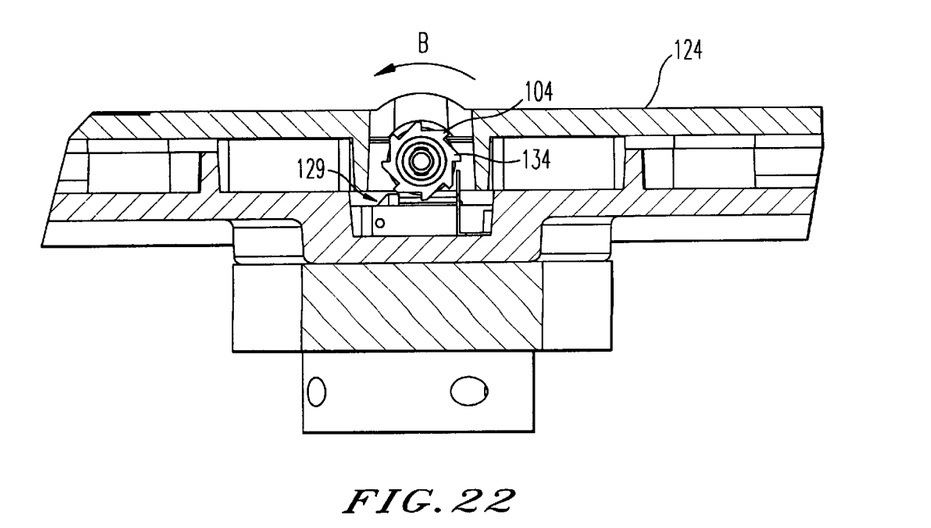
FIG. 22 is a cross-sectional view of the carrier tube system as loaded in the rotor as taken along lines 22—22 in FIG. 4.

FIG. 22 is a cross-sectional view taken along line 22—22 in FIG. 4, illustrating the relationship of the cap to an indexing mechanism 129 of the rotor 124. The indexing mechanism 129 engages the teeth 134 to rotate the cap 104, and hence the tube carrier system 100, as a whole, in the direction as indicated by the arrow B. This enables the optical reading device (not shown) of the centrifuge device 120 to take layer thickness readings of the centrifuged blood in the capillary tube 114 at different positions around the circumference of the capillary tube 114. The operation of the indexing mechanism 129 and optical reading device are described in more detail in the aforementioned copending U.S. patent application of Michael R. Walters entitled "Inertial Tube Indexer", Ser. No. 09/032,931, and in the aforementioned copending U.S. patent application of Bradley S. Thomas et al. entitled "Blood Centrifugation Device with Movable Optical Reader", Ser. No. 09/033,368.

Other embodiments of the carrier tube system 100 are also possible. In particular, the cap and float holder can have a modified configuration as shown, for example, in FIG. 23. Specifically, the carrier tube system 200 shown in FIG. 23 has a cap 204 which does not include any gear teeth as does cap 104 in the tube holder system 100 of FIGS. 1–22. As further shown in FIG. 24, the float holder 206 can have a configuration different from that of float holder 106. Specifically, the float holder 206 has outer resilient members 207 that are integral with inner resilient members 208. When a float 108 is inserted in an opening 209 formed by the resilient inner members 208, the resilient inner members 208 hold the float 108 in place in a manner similar to that in which sections 144 of the float holder 106 hold the float 108 in place as described above. The resilient outer members 207 of the float holder 206 deform slightly when the float 108 is inserted into the cap 204, to thereby hold the float holder 206 in the cap as shown in FIG. 23.

Figure 23:
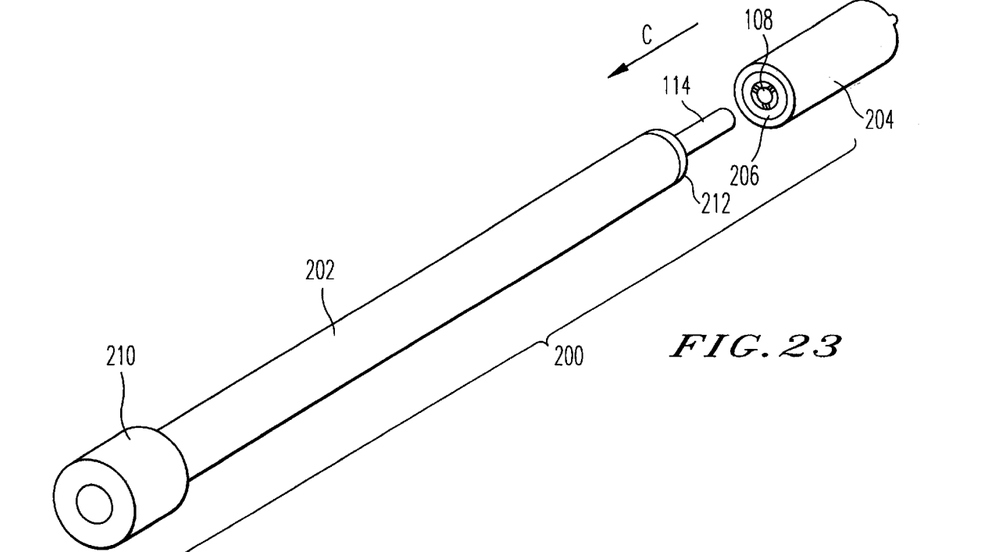
FIG. 23 is an exploded perspective view of an example of a carrier tube system according to another embodiment of the present invention having a float holder configured differently than the float holder of the system shown in FIG. 1.

As further shown in FIG. 23, the carrier tube system 200 includes a carrier tube 202 which is similar in construction to carrier tube 102, and a top collar 212 that is similar in construction to top collar 112. However, the top collar 212 can have any suitable construction which will enable it to secure the capillary tube 114 in the carrier tube 202.

The bottom plug 210 of FIG. 23 has a configuration different from that of bottom plug 110 in the carrier tube system 100. In particular, the bottom plug 210 has a recess which receives the bottom of the carrier tube 202 therein. The bottom plug 210 also has a portion similar or identical to the portion 154 of bottom plug 110, which secures the capillary tube 114 in the carrier tube 202 in a manner similar to that in which the bottom plug 110 secures the capillary tube 114 in the carrier tube 102 as described above. However, in the arrangement of FIGS. 23 and 24, the cap 204 does not couple to the bottom of the carrier tube 202, and hence to the bottom plug 210, when the carrier tube system 200 is sterilized and packaged for transfer to a laboratory. Rather, the cap 204 is a separate component which is inserted onto the top of the carrier tube 202 in a manner similar to that in which the cap 104 is inserted onto the top of carrier tube 102 after blood has been received into the capillary tube 114. However, the bottom plug 210 can be configured such that the cap 204 couples to the bottom plug 210 when the carrier tube system 200 is packaged for transportation to a laboratory where it will be used to collect the blood sample.

Figure 24:
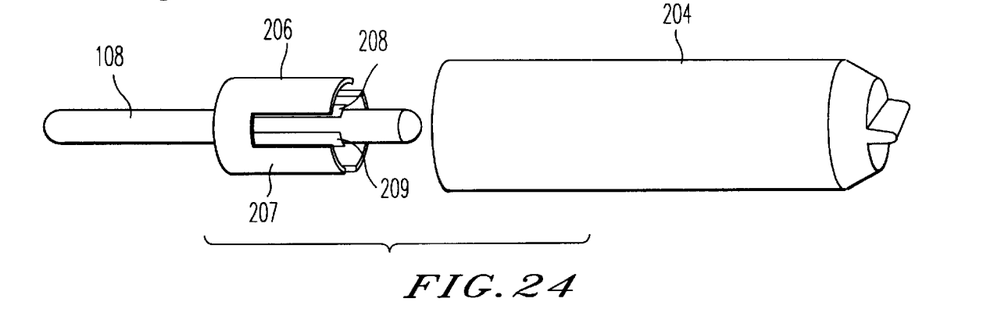
FIG. 24 is a detailed perspective view of the cap, float and float holder of the system as shown in FIG. 23.

When the cap 204 of FIGS. 23 and 24 is inserted onto the top of the carrier tube 202, the float holder 206 operates in a manner similar to float holder 106 to enable the float 108 to be automatically inserted into the capillary tube 114. That is, the resiliently deflectable inner members 208 will be deflected by the capillary tube 114 as the float 108 is being inserted into the capillary tube 114. Furthermore, the top collar 112 will contact the float holder 206 and push the float holder further into the cap 204 when the cap is moved onto the carrier tube 202 in the direction indicated by arrow C in FIG. 23. The float holder 206 also acts as a limiting device which limits the depth at which the carrier tube 202 can be inserted into the cap 204 in a manner similar to float holder 106 as discussed above.

When the cap 204 has been completely installed on the carrier tube 202, the carrier tube system 200 is in its capped configuration. The carrier tube system 200 can then be used with a centrifuge device 120 having a rotor 124 which is capable of accommodating and rotating a carrier tube system 200 that does not have a geared portion formed on its cap 204. This type of rotor is further described in the aforementioned copending U.S. patent application of Michael R. Walters entitled "Inertial Tube Indexer", Ser. No. 09/032,931.

As a further modification, the caps 104 and 204 of the carrier tube systems 100 and 200 can be configured so that they do not accommodate a float holder and float. Rather, in these modified arrangements, the float can be inserted manually into the capillary tube 114 after the blood sample has been received in the capillary tube 114. The cap can then be placed onto the carrier tube, and the capped carrier tube system can be centrifuged in the centrifuge device 120.

Figure 25:
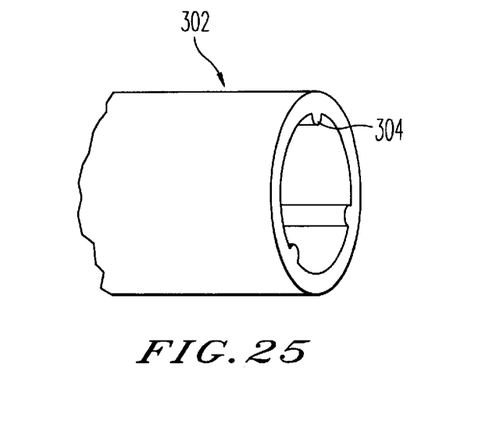
FIG. 25 is a detailed perspective view of an alternate configuration of the carrier tube of the systems shown in FIGS. 1 and 23.
Figure 26:
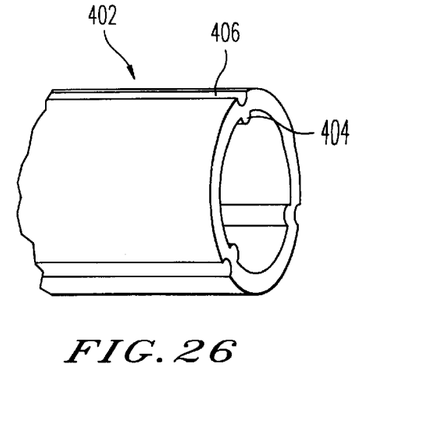
FIG. 26 is a detailed perspective view of another example of an alternate configuration of the carrier tube of the systems shown in FIGS. 1 and 23.

In a further modification shown in FIG. 25, the carrier tube 302 includes internal ribs 304 which extends longitudinally along the entire length (or any portion of the length) of the carrier tube 302. The internal ribs 304 assist in centering and stabilizing the capillary tube 114 in the carrier tube 302. Alternatively, as shown in FIG. 26, the carrier tube 402 can include internal ribs 404 and external ribs 406 which extend longitudinally along the entire length (or any portion of the length) of the carrier tube 402. The mold (not shown) used for forming the carrier tube 402 can be configured to form the external ribs 406 to maintain proper flow of the plastic material. Furthermore, the external ribs 406 can be read by the optical reading device (not shown) of the centrifuge device 120 of FIGS. 3 and 4 to detect the orientation of the carrier tube 402 as the carrier tube is being rotated about its longitudinal axis by the indexing mechanism of the centrifuge device 120.

Although only a few exemplary embodiments of this invention have been described in detail above, those skilled in the art will readily appreciate that many other modifications are possible without materially departing from the novel teachings and advantages of the invention. Accordingly, all such modifications are intended to be included within the scope of the invention as defined in the following claims.

What is claimed is:

1. A carrier system for use with a blood tube, comprising:
   a carrier tube having a chamber therein and an opening at a first end thereof for providing access to the chamber, the chamber being configured to receive a blood tube therein through the opening; and
   a cap adapted to be coupled to the first end of the carrier tube to substantially isolate the blood tube from the outside of the carrier tube, wherein the cap includes a float which is removably coupled thereto, such that the float enters the blood tube when the cap is coupled to the first end of the carrier tube.

2. A carrier system as claimed in claim 1, wherein the cap includes gear teeth, adaptable to engage with a drive mechanism of a centrifuge device, to enable the drive mechanism to rotate the carrier system about its longitudinal axis.

3. A carrier system as claimed in claim 1, wherein the carrier tube further comprises a blood tube holding device, adapted to hold the blood tube at a first position before the cap is coupled to the first end of the carrier tube, and to permit the blood tube to move longitudinally in the chamber of the carrier tube when the cap is coupled to the first end of the carrier tube.

4. A carrier system as claimed in claim 3, wherein:
   the blood tube holding device holds the blood tube at the first position before the cap is coupled to the first end of the blood tube to permit gas passing out of an opening in the blood tube, when blood is being received in the blood tube, to flow into the chamber of the carrier tube;
   the carrier tube further comprises a sealing device for sealing said opening; and
   the blood tube holding device permits the blood tube to move longitudinally in the chamber of the carrier tube when the cap is coupled to the first end of the carrier tube to enable the sealing device to seal the opening in the blood tube.

5. A system as claimed in claim 1, wherein the cap comprises a limiting device adapted to limit insertion of the carrier tube into the cap upon fracture of the blood tube after the cap has been coupled to the first end of the carrier tube.

6. A fluid tube system, adaptable for use with a centrifuge device, comprising:
   a carrier tube having a chamber therein and an opening providing access to the chamber;
   a capillary fluid tube insertable into the chamber of the carrier tube through the opening, and having an interior chamber for receiving fluid; and
   a cap adapted to be coupled to a first end of the carrier tube to substantially isolate the interior chamber of the fluid tube from the outside of the carrier tube, wherein the cap includes a float which is removably coupled thereto, such that the float enters the interior chamber of the fluid tube when the cap is coupled to the end of the carrier tube.

7. A fluid tube system as claimed in claim 6, wherein the cap includes gear teeth adaptable to engage with a drive mechanism of a centrifuge device, to enable the drive mechanism to rotate the fluid tube system about its longitudinal axis.

8. A fluid tube system as claimed in claim 6, wherein the carrier tube further comprises an fluid tube holding device adapted to hold the fluid tube at a first position before the cap is coupled to the first end of the carrier tube, and to permit the fluid tube to move longitudinally in the chamber of the carrier tube when the cap is coupled to the first end of the carrier tube.

9. A fluid tube system as claimed in claim 6, wherein the cap comprises a limiting device adapted to limit insertion of the carrier tube into the cap upon fracture of the fluid tube after the cap has been coupled to the first end of the carrier tube.

10. A fluid tube system as claimed in claim 6, wherein the fluid tube includes a plug in the interior chamber thereof, the plug having an opening therein to permit the passage of gas from the interior chamber of the fluid tube when fluid is received in the interior chamber of the fluid tube.

11. A fluid tube system as claimed in claim 10, wherein the carrier tube further comprises:

a fluid tube holding device, configured to hold the fluid tube at a first position before the cap is coupled to the first end of the carrier tube, and to permit the gas passing out of the opening in the fluid tube to flow into the chamber of the carrier tube; and a sealing device for sealing said opening;

the fluid tube holding device being further adapted to permit the fluid tube to move longitudinally in the chamber of the carrier tube when the cap is coupled to the first end of the carrier tube to enable the sealing device to seal the opening in the plug.

12. A cap adapted to be coupled to a carrier tube for a capillary tube, comprising:

a cap body having a cavity therein;

a float adapted to be inserted into the capillary tube; and a float holder adapted to be inserted into the cavity of the cap body and to releasably hold the float in the cavity when inserted into the cavity.

13. A cap as claimed in claim 12, wherein the float holder is adapted to release the float into the capillary tube upon contact with the capillary tube when the cap is coupled to the carrier tube.

14. A cap as claimed in claim 12, wherein the float holder is adapted to contact a portion of the carrier tube to be moved in the cavity of the cap when the cap is coupled to the carrier tube.

15. A cap as claimed in claim 12, wherein the float holder is adapted to limit insertion of the carrier tube into the cavity of the cap in the event that the capillary tube fractures.

16. A carrier system for use with a blood tube, comprising:

a carrier tube having a chamber therein and an opening at a first end thereof for providing access to the chamber, the chamber being configured to receive a blood tube therein through the opening; and a cap adapted to be coupled to the first end of the carrier tube to substantially isolate the blood tube from the outside of the carrier tube, wherein the cap is adapted to be coupled to a second end of the carrier tube to allow access to the blood tube when the blood tube is positioned in the chamber of the carrier tube, and further wherein the cap includes a float which is removably coupled thereto, such that the float remains in the cap when the cap is coupled to the second end of the carrier tube, and enters the blood tube when the cap is coupled to the first end of the carrier tube.

17. A fluid tube system, adaptable for use with a centrifuge device, comprising:

a carrier tube having a chamber therein and an opening providing access to the chamber;

a capillary fluid tube insertable into the chamber of the carrier tube through the opening, and having an interior chamber for receiving fluid; and a cap adapted to be coupled to a first end of the carrier tube to substantially isolate the interior chamber of the fluid tube from the outside of the carrier tube, wherein the cap is adapted to be coupled to a second end of the carrier tube to allow access to the interior chamber of the fluid tube when the fluid tube is positioned in the chamber of the carrier tube, and further wherein the cap includes a float which is removably coupled thereto, such that the float remains in the cap when the cap is coupled to the second end of the carrier tube, and enters the interior chamber of the fluid tube when the cap is coupled to the first end of the carrier tube.

* * * * *